(12) United States Patent
Visser

(10) Patent No.: US 6,935,166 B1
(45) Date of Patent: Aug. 30, 2005

(54) MEASUREMENT OF MOISTURE OF POTTING SOIL

(75) Inventor: Cornelis F. T. Visser, 's-Gravendeel (NL)

(73) Assignee: Visser's-Gravendeel Holding B.V., S'Gravendeel (NL)

( * ) Notice: Subject to any disclaimer, the term of this patent is extended or adjusted under 35 U.S.C. 154(b) by 0 days.

(21) Appl. No.: 10/070,384

(22) PCT Filed: Sep. 1, 2000

(86) PCT No.: PCT/NL00/00609

§ 371 (c)(1),
(2), (4) Date: Jul. 9, 2002

(87) PCT Pub. No.: WO01/19165

PCT Pub. Date: Mar. 22, 2001

(30) Foreign Application Priority Data

Sep. 15, 1999 (NL) .................................. 1013057

(51) Int. Cl.[7] ............................................. G01N 5/02
(52) U.S. Cl. ............................. 73/73; 73/74; 324/640; 324/643
(58) Field of Search ...................... 73/73, 74; 324/640, 324/643

(56) References Cited

U.S. PATENT DOCUMENTS

| | | | |
|---|---|---|---|
| 2,665,409 A * | 1/1954 | Rogers ..................... | 73/863.51 |
| 4,403,191 A * | 9/1983 | Satake ....................... | 324/452 |
| 4,590,795 A * | 5/1986 | Oetiker et al. .............. | 73/73 |
| 4,652,811 A | 3/1987 | Kwiat et al. | |
| 4,675,595 A * | 6/1987 | Hane ........................... | 324/640 |
| 5,006,225 A * | 4/1991 | Beauchemin et al. .......... | 73/73 |
| 5,685,772 A * | 11/1997 | Andersen et al. .............. | 460/6 |
| 6,068,059 A * | 5/2000 | Bajema et al. .............. | 171/130 |
| 6,078,181 A * | 6/2000 | Robichaud et al. ............ | 73/73 |
| 6,210,727 B1 * | 4/2001 | Miller et al. ................. | 73/433 |
| 6,281,801 B1 * | 8/2001 | Cherry et al. ................ | 340/605 |
| 6,440,475 B1 * | 8/2002 | McNeff et al. ................ | 73/73 |

FOREIGN PATENT DOCUMENTS

| | | |
|---|---|---|
| EP | 0853074 A | 7/1998 |
| JP | 08-242683 A | 9/1996 |
| JP | 08-280267 A | 10/1996 |
| RU | 2046325 C | 10/1995 |

* cited by examiner

*Primary Examiner*—Hezron Williams
*Assistant Examiner*—André K. Jackson
(74) *Attorney, Agent, or Firm*—Harness, Dickey & Pierce, P.L.C.

(57) ABSTRACT

The invention relates to a method and apparatus for determining the moisture content of bulk material, in particular potting soil, wherein the volume of a quantity of bulk material is determined, the weight of the quantity of bulk material is determined, the specific density is then determined from the volume and the weight, and finally the moisture content is determined by comparison with a table. The invention further relates to a method and apparatus for preparing bulk material, in particular potting soil, with a predetermined moisture content, wherein the volume of a quantity of bulk material is determined, the weight of the quantity of bulk material is determined, and water is then added to the quantity of bulk material until the weight associated with the desired moisture content is obtained.

17 Claims, 1 Drawing Sheet

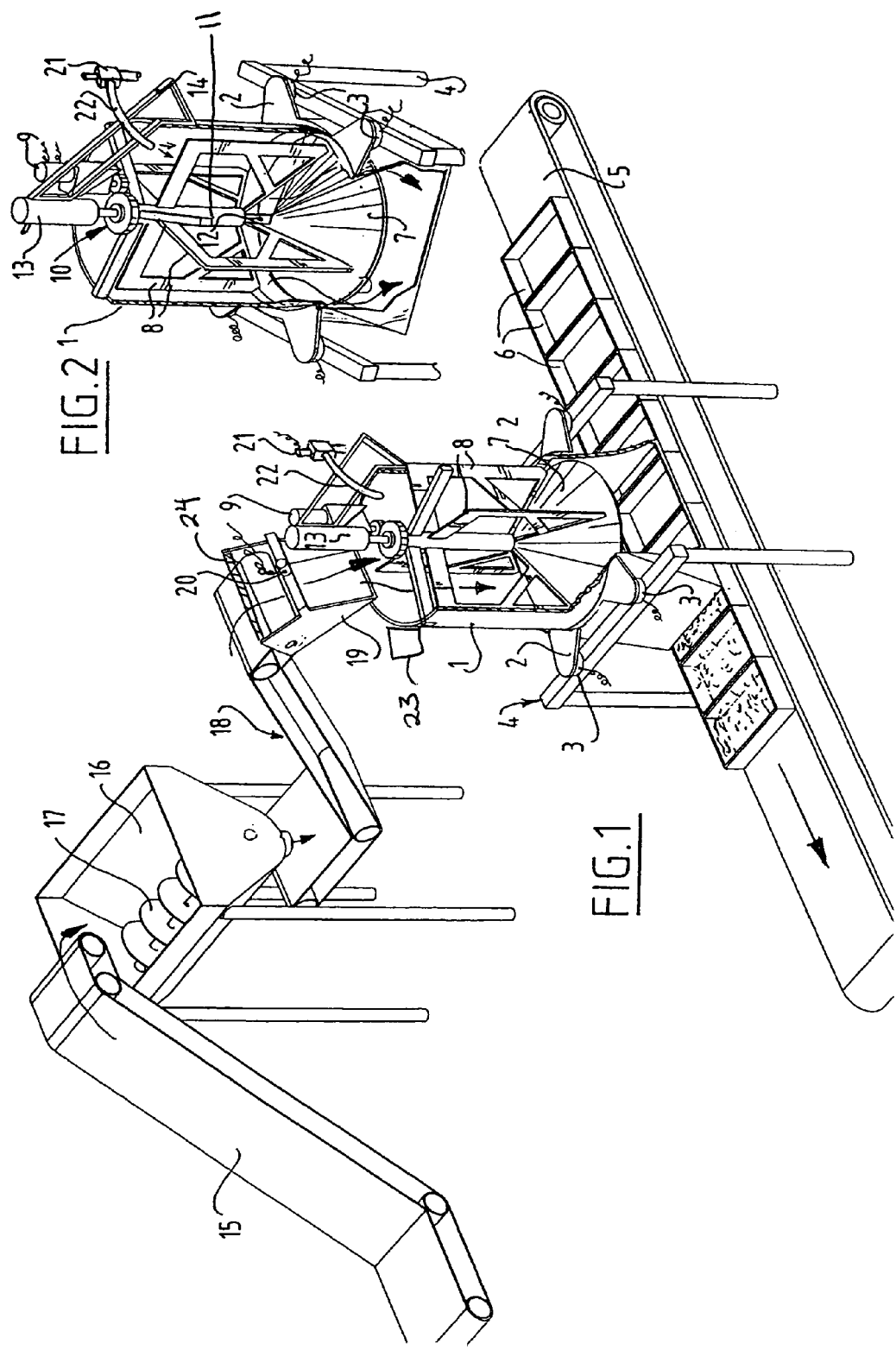

US 6,935,166 B1

MEASUREMENT OF MOISTURE OF POTTING SOIL

CROSS REFERENCE TO RELATED APPLICATIONS

This is a U.S. National Phase Application under 35 U.S.C. § 371 and applicant herewith claims the benefit of priority of PCT/NL00/00609 filed Sep. 1, 2000, which was published Under PCT Article 21(2) in English, which claims priority to Dutch Application No. 1013057, filed Sep. 15, 1999, the entire contents of which are incorporated herein by reference.

FIELD OF THE INVENTION

The present invention relates to a method and apparatus for determining the moisture content of bulk material, in particular growing substrate such as potting soil.

BACKGROUND OF THE INVENTION

With the increased mechanization in horticulture it is important to manage the processing conditions for the plants as well as possible. One condition which has been poorly managed heretofore is the moisture content of growing substrate such as potting soil. When wholly artificial substrates such as mineral wool and the like are used, it is possible to properly determine and manage the moisture content thereof. In the case of potting soil and mixtures of potting soil this is however much more difficult; the composition of the potting soil is much more heterogeneous and moreover varies, while the water-retaining properties of potting soil are difficult to establish. The water content of potting soil is moreover highly variable, particularly if it has been stored for some time in the outside air.

There therefore exists a need for a method and apparatus for determining the moisture content of potting soil. There is furthermore a need for a method and an apparatus for correcting the moisture content, in particular for increasing the moisture content to a predetermined value.

BRIEF DESCRIPTION OF THE INVENTION

These objectives are achieved by a method which is characterized in that the volume of a quantity of bulk material, in particular growing substrate such as potting soil, is determined, the weight of the quantity of bulk material is determined, the specific density is then determined from the volume and the weight, and finally the moisture content is determined by comparison with a table.

The present invention further provides such a method for preparing bulk material, in particular growing substrate such as potting soil, with a predetermined moisture content, which is characterized in that the volume of a quantity of bulk material is determined, the weight of the quantity of bulk material is determined, and water is then added to the quantity of bulk material until the weight associated with the desired moisture content is obtained.

The invention also provides for this purpose an apparatus for determining the moisture content of bulk material, in particular potting soil, which apparatus is characterized in that it comprises:
 a supply vessel placed on a weighing device;
 a feed device for feeding predetermined volumes to the supply vessel;
 a discharge device for the supply vessel; and
 a computer for determining the moisture content from the supplied volume and the measured weight.

Finally, the present invention provides such an apparatus which is characterized in that the feed device comprises a conveyor belt which comprises a measuring member for measuring the height of the bulk material carried along on the conveyor belt, and wherein the computer is adapted to determine from the measured height the quantity of material carried along on the conveyor belt.

Other attractive preferred embodiments are stated in the sub-claims.

BRIEF DESCRIPTION OF THE DRAWINGS

The present invention will be elucidated hereinbelow with reference to:

FIG. 1, which shows a partly broken-away perspective view of an apparatus according to the present invention; and FIG. 2, which shows a perspective detail view of such an apparatus.

DETAILED DESCRIPTION OF THE INVENTION

FIG. 1 shows a vessel 1 provided on its underside with four protrusions 2. Each of the four protrusions 2 rests by means of a pressure sensor 3 on a frame 4. A conveyor belt 5 is arranged under the frame to transport the containers for filling, in this case boxes 6.

A stirring gear 8 is arranged in the vessel, which is provided with a conical bottom 7. Stirring gear 8 can be driven by means of an electric motor 9 shown clearly in FIG. 2 which drives a central shaft 11 of stirring gear 8 by means of a gear transmission 10. Arranged inside the central shaft 11 of the stirring gear is a control shaft 12 which is non-rotatable but movable in vertical direction and which can move the conical bottom 7 upward and downward when driven by a linear drive element 13. This latter is connected to the outside is of vessel 1 by means of a frame 14. The up and downward movement of the conical bottom has the purpose of emptying vessel 1.

For supplying of potting soil use is made of a second conveyor belt 15 for bulk material. The second conveyor belt 15 leads to a mixing vat 16 where the supplied material is reduced in size by means of a screw 17 and homogenized as well as possible. From mixing vat 16 the potting soil comes to lie on a third conveyor belt 18, which leads via a chute 19 to the top side of vessel 1. A laser measuring device 20 is arranged on chute 19 for measuring the height of the supplied strip of potting soil. According to the shown embodiment the laser height measuring device 20 is provided with a laser head which determines the height of the supplied quantity of soil by means of a repetitive swinging movement. It is possible to make use of other types of laser measuring devices, for instance provided with a leveling device 24.

Arranged for supplying water is a controllable tap 21 which is connected by means of a spout 22 to the content of vessel 1.

The operation of the present invention will now be described during performing of the method according to the present invention.

Assuming that vessel 1 is empty, soil is fed to vessel 1 via conveyor belts 15, mixing vat 16, the third conveyor belt 18 and chute 19. The volume of soil supplied is herein determined by means of the integrating laser height measuring device. When a desired volume quantity has been supplied, the feed of potting soil is stopped and the weighing device formed by pressure sensors 3 is activated. The weight resulting herefrom is carried to a measuring computer, not shown in the drawings, whereafter the computer determines the density of the quantity of potting soil on the basis of the weight. It is hereby possible, and with reference to a for instance empirically formulated table, to determine the moisture content of the potting soil. It is herein possible to employ different types of tables for different types of potting soil.

It will usually be the desire not only to know the density of the potting soil but also to correct it. If the potting soil is too dry, it is easy to add water. For this purpose the control device is connected to a tap 21 with which it is possible to feed a predetermined volume of water to vessel 1. Stirring gear 8 can then be activated to make a homogeneous mixture. It will be apparent that it is only possible to moisten potting soil which is too dry; the reverse procedure is of course not possible. It is however possible to mix the moist potting soil with dry potting soil from another source. In order to make this possible the components indicated with reference numerals 15–20 will have to be duplicated.

Once an homogeneous mixture has been obtained by the action of stirring gear 8, the bottom 7 is moved downward by means of linear drive device 13, whereafter the released soil can be poured into containers 6 in per se known manner. Once vessel 1 is empty, the whole process can be repeated.

It will be apparent that with the use of a computer countless variations of the described method can be applied.

It is thus possible to make use of a drag chain. Such a chain extends in lengthwise direction of the chute. Mounted at regular distances on such a chain are carriers which are each suitable for carrying along a predetermined quantity of bulk material as the chain with the carriers moves along the chute.

It is pointed out here that the computer usually fulfils a particular function in determining the volume by integrating the signals originating from the laser height measuring device 20.

It is further possible to arrange a dispensing device 23 on the mixing vat in order to add additives such as fertilizer, pesticides/herbicides and so on to the growing substrate.

What is claimed is:

1. Method for determining the moisture content of a quantity of soil comprising:
   determining the volume of the quantity of soil,
   determining the weight of the quantity of soil,
   determining the specific density from the volume and the weight, and
   finally determining the moisture content by comparing the specific density with a table containing moisture content and specific density information for the soil.

2. Method for preparing a quantity of soil with a predetermined moisture content comprising
   determining the volume of the quantity of soil,
   determining the weight of the quantity of soil,
   determining the specific density of the quantity of soil from the volume and weight,
   determining the moisture content of the quantity of soil,
   calculating the additional amount of water necessary to obtain the predetermined moisture content of the quantity of soil, and
   adding water to the quantity of soil until the weight associated with the desired moisture content is obtained.

3. Method as claimed in claim 2 further comprising, after adding the water, mixing the soil with the water.

4. Apparatus for determining the moisture content of soil comprising:
   a supply vessel placed on a weighing device to obtain a measured weight of the soil;
   a feed device for feeding predetermined volumes of soil to the supply vessel;
   a discharge device to release the soil from the supply vessel; and
   a computer for determining the moisture content from the predetermined volume and the measured weights
   wherein the feed device comprises a conveyor belt.

5. Apparatus as claimed in claim 4 wherein the feed device comprises further comprises a measuring member for measuring the height of the soil carried along on the conveyor belt, and that the computer is adapted to determine from the measured height the quantity of soil carried along on the conveyor belt.

6. Apparatus as claimed in claim 5 wherein the measuring member comprises a laser source and a laser detector, wherein these elements are adapted to determine the height of the material carried along on the conveyor belt.

7. Apparatus as claimed in claim 5 further comprising a leveling device placed above the conveyor belt upstream of the measuring member for leveling to a uniform height the material carried along on the conveyor belt.

8. Apparatus as claimed in claim 4 wherein the supply vessel is tiltable.

9. Apparatus as claimed in claim 4 wherein the apparatus is also suitable for preparing soil with the desired moisture content in that a water supply device is placed above the supply vessel in order to supply water to the supply vessel.

10. Apparatus as claimed claim 4 wherein the apparatus is provided with a dispensing device for dispensing additives.

11. Apparatus as claimed in claim 6 further comprising a leveling device placed above the conveyor belt upstream of the measuring member for leveling to a uniform height the material carried along on the conveyor belt.

12. Apparatus as claimed in claim 5 wherein the supply vessel is tiltable.

13. Apparatus as claimed in claim 6 wherein the supply vessel is tiltable.

14. Apparatus as claimed in claim 7 wherein the supply vessel is tiltable.

15. Apparatus as claimed in claim 7 wherein the apparatus is also suitable for preparing soil with the desired moisture content in that a water supply device is placed above the supply vessel in order to supply water to the supply vessel.

16. Apparatus as claimed claim 6 wherein the apparatus is provided with a dispensing device for dispensing additives.

17. Apparatus as claimed claim 9 wherein the apparatus is provided with a dispensing device for dispensing additives.

* * * * *